Sept. 14, 1976 R. L. SUMRULD Plant Pat. 3,949
PLUM TREE
Filed Aug. 15, 1975
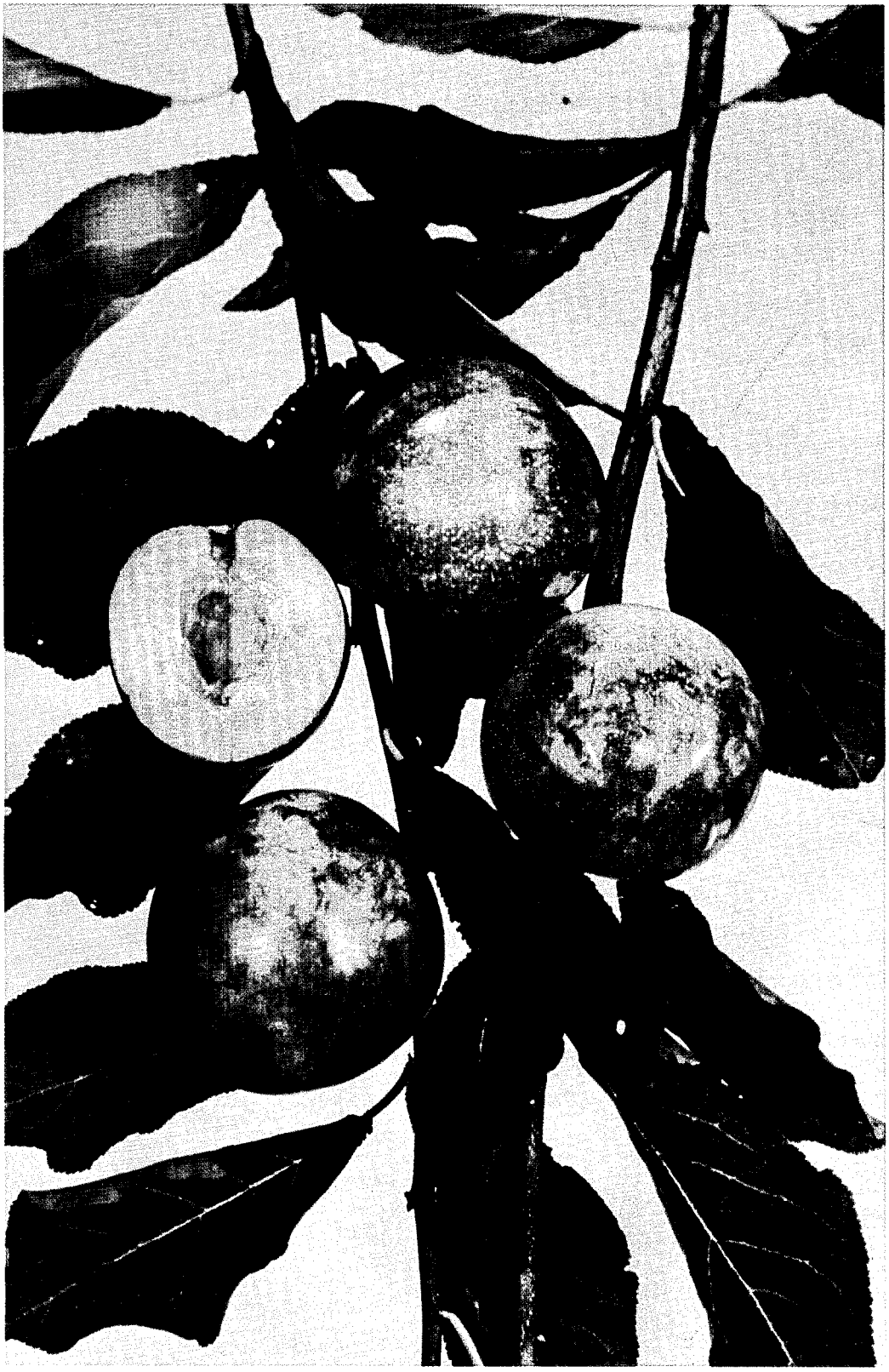

United States Patent

Plant Pat. 3,949

Patented Sept. 14, 1976

3,949

PLUM TREE

Roy Lester Sumruld, 452 E. Merritt, Tulare, Calif. 93274

Filed Aug. 15, 1975, Ser. No. 604,909

Int. Cl.[2] A01H *5/03*

U.S. Cl. Plt.—38 1 Claim

ABSTRACT OF THE DISCLOSURE

The present invention pertains to an improved variety of plum tree, capable of bearing high quality fruit at regular intervals. The fruit is of a late ripening variety maturity being reached around Aug. 23, approximately 12 to 15 days later than the unpatented Casselman tree and considerably earlier than the Roysum tree (Plant Pat. 2,619) which matures around Oct. 13.

BACKGROUND OF THE INVENTION

The plum tree which is the subject of the present invention was discovered in Tulare County, in the State of California and was observed in the form of a sport limb growing from a Roysum plum tree (Plant Pat. 2,619) planted on the inventor's farm. Continued observation of the sport limb disclosed that the fruit thereon ripened considerably prior to fruit typically grown on a Roysum tree.

Since observing the sport limb, the inventor has grafted more than 20 trees from cuttings made from the aforesaid limb and the grafts have displayed the characteristics of the sport limb. During 1974, fruit was first picked from the grafted trees on or about Aug. 23, 1974 and the date of last picking was on or about Aug. 30, 1974.

The accompanying drawing is a color photograph of a characteristic twig of the subject plum tree bearing foliage and exemplars of the mature fruit typifying the present invention. One of such exemplars has been divided on its suture plane to reveal typical flesh coloration and pit characteristics.

Having thus described the observed characteristics of the tree of the present invention, the following pomological details pertaining to this new and improved variety of plum tree, as grown and observed under the prevailing climatic conditions in Tulare County, Calif., are as follows:

(All major color plate identifications are by reference to the British Horticultural Colour Chart.)

Tree

Size: Large, vigorous, upright, vase formed by pruning, productive, and regular bearer.

Trunk: Medium-slender, shaggy, rough bark, brownish-grey. Lenticels—numerous, medium.

Leaves (selected from midportion of vigorous unbranched terminal shoots):

*Length.*—Mature leaf—up to 4".

*Width.*—Mature leaf—varies from 1 7/16" to 1¾".

*Form.*—Lanceolate to broad lanceolate.

*Color.*—Upper surface—dark green. Vein color. Lower surface—dark green but lighter and more dull than upper surface.

*Margin.*—Serrated.

*Petiole.*—½ to ⅝" in length, medium in thickness.

*Glands.*—None on most—1–3 on largest leaves. Average number 1–3, alternate, small, reniform, green (dark green to dark brown), position—petiole and base of leaf.

Fruit

Maturity when described: Firm ripe, date Aug. 23, 1974—about 12 to 15 days later than Casselman.

Size: Variable, large, medium. Diameter—average 5 centimeters (2⅛"). Transverse in suture plane—5 centimeters (2⅛"). Transverse at right angles to suture plane—average diameter slightly less than 2⅛".

Form: Quite uniform, symmetrical.

Suture: 7–8 centimeters.

Ventral surface: Smooth.

Cavity: Uniform shape, not overly deep, rather small.

Base: Rounded.

Apex: Rounded, slightly flattened.

Pistil point: Very small, inconspicuous.

Stem:

*Length.*—Short to very short, moderate diameter but quite adequate.

Skin: Moderate, firm not easily bruised.

*Tendency to crack.*—Average—not excessive.

*Color.*—Yellow overlaid with red (near ruby red). 827/2 at darkest. Color may vary from yellow (straw yellow) overlaid with red to all red (as above).

*Pubescence.*—Moderate, similar to Santa Rosa.

Flesh:

*Color.*—Amber yellow with no other color around pit or bleeding from skin.

*Pit well.*—Amber yellow.

*Juice.*—Flesh solid with little juice.

*Texture.*—Very solid.

*Fibers.*—Not noticeable.

*Ripens.*—Quite even.

*Flavor.*—Pleasant, tart/sweet—sprightly.

*Eating quality.*—Excellent.

Stone: Cling.

*Adheres to flesh.*—No open spaces around pit.

*Fibers.*—Numerous, holding pit lightly to flesh.

*Size.*—Small in relation to fruit.

*Form.*—Oval, somewhat flattened with acute tip.

*Base.*—Rounded.

*Sides.*—Relatively smooth.

*Color of stone.*—Darker than flesh.

*Tendency to split.*—Not observed, well sealed.

Use: Fresh, dessert, eating out of hand.

Keeping quality: Excellent.

Shipping quality. Good.

Thus, the present invention is characterized by the provision of a firm, pleasant and tart/sweet fruit having characteristics which make it easily shippable by commercial means to distant markets during a period when the Casselman and Santa Rosa plums have been already marketed and well before the Roysum plum is ready for market.

Accordingly, the instant invention provides a commercially desirable cultivar of plum which matures at a time which permits it to be marketed during a period when other plum varities of comparable quality have either already been marketed, and the supply exhausted, or not yet mature. The grower is, therefore, provided with a high quality product which may be marketed throughout the United States during a high demand period.

The invention claimed is:

1. A new and distinct variety of plum substantially as described and illustrated, and having as a principal distinguishing characteristic its ripening to maturity approximately 12 to 15 days subsequent to the Casselman (unpatented) plum tree and more than six weeks earlier than the Roysum (patented) plum tree.

No references cited.

ROBERT E. BAGWILL, Primary Examiner